United States Patent
Windmiller

(10) Patent No.: US 11,406,818 B2
(45) Date of Patent: Aug. 9, 2022

(54) TISSUE-PENETRATING ELECTROCHEMICAL SENSOR FEATURING A CO-ELECTRODEPOSITED THIN FILM COMPRISED OF POLYMER AND BIO-RECOGNITION ELEMENT

(71) Applicant: Biolinq Incorporated, San Diego, CA (US)

(72) Inventor: Joshua Windmiller, Del Mar, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 16/666,259

(22) Filed: Oct. 28, 2019

(65) Prior Publication Data

US 2020/0085341 A1 Mar. 19, 2020

Related U.S. Application Data

(63) Continuation of application No. 16/152,372, filed on Oct. 4, 2018, now Pat. No. 10,492,708, which is a
(Continued)

(51) Int. Cl.
*A61N 1/30* (2006.01)
*A61N 1/05* (2006.01)
(Continued)

(52) U.S. Cl.
CPC .............. *A61N 1/30* (2013.01); *A61B 5/05* (2013.01); *A61B 5/1468* (2013.01);
(Continued)

(58) Field of Classification Search
CPC .......... A61N 1/30; A61B 5/05; A61B 5/14546
See application file for complete search history.

(56) References Cited

U.S. PATENT DOCUMENTS

| 4,305,401 A | 12/1981 | Reissmueller et al. |
| 4,323,996 A | 4/1982 | Ganter |

(Continued)

FOREIGN PATENT DOCUMENTS

| CN | 101915794 A | 12/2010 |
| KR | 10-2016-0108111 A | 9/2016 |

(Continued)

OTHER PUBLICATIONS

Abbot press release (2020). "New late-breaking data show use of abbott's Freestyle® Libre System significantly reduces HBA1C levels in people with type 2 diabetes using insulin or not," 3 pages.
(Continued)

*Primary Examiner* — Olatunji A Godo
(74) *Attorney, Agent, or Firm* — Cooley LLP

(57) ABSTRACT

A method and device to impart the ability to selectively quantify chemical/biochemical analytes occupying physiological fluids via an automated process that allow the precise and spatially-defined simultaneous deposition of a thin-film of polymer containing an immobilized biorecognition element dispersed therein. A tissue penetrating electrochemical sensor comprises at least one working electrode and at least one of a reference electrode and a counter electrode.

19 Claims, 8 Drawing Sheets

Related U.S. Application Data continuation of application No. 15/590,105, filed on May 9, 2017, now Pat. No. 10,092,207.

(60) Provisional application No. 62/336,724, filed on May 15, 2016.

(51) Int. Cl.
　　*A61B 5/1468*　　(2006.01)
　　*A61B 5/05*　　(2021.01)
　　*A61B 5/145*　　(2006.01)
　　*A61M 5/172*　　(2006.01)

(52) U.S. Cl.
　　CPC ....... *A61B 5/14546* (2013.01); *A61M 5/1723* (2013.01); *A61N 1/05* (2013.01); *A61B 2562/125* (2013.01); *Y02E 60/50* (2013.01)

(56) References Cited

U.S. PATENT DOCUMENTS

| | | | |
|---|---|---|---|
| 4,407,295 A | 10/1983 | Steuer et al. |
| 4,450,842 A | 5/1984 | Zick et al. |
| 4,756,807 A | 7/1988 | Meyer et al. |
| 4,908,117 A | 3/1990 | Kinlen et al. |
| 5,131,390 A | 7/1992 | Sakaguchi et al. |
| 5,166,063 A | 11/1992 | Johnson |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 6,036,055 A | 3/2000 | Mogadam et al. |
| 6,132,449 A | 10/2000 | Lum et al. |
| 6,139,718 A | 10/2000 | Kurnik et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,471,903 B2 | 10/2002 | Sherman et al. |
| 6,603,987 B2 | 8/2003 | Whitson |
| 6,793,789 B2 | 9/2004 | Choi et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,097,776 B2 | 8/2006 | Govinda Raju |
| 7,132,054 B1 | 11/2006 | Kravitz et al. |
| 7,169,284 B1 | 1/2007 | Jiang et al. |
| 7,220,550 B2 | 5/2007 | Keen |
| 7,262,068 B2 | 8/2007 | Roy et al. |
| 7,343,188 B2 | 3/2008 | Sohrab |
| 7,344,499 B1 | 3/2008 | Prausnitz et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,473,244 B2 | 1/2009 | Frazier et al. |
| 7,493,232 B1 | 2/2009 | Surina |
| 7,837,654 B2 | 11/2010 | Shumate et al. |
| 7,949,382 B2 | 5/2011 | Jina |
| 8,005,526 B2 | 8/2011 | Martin et al. |
| 8,022,292 B2 | 9/2011 | Arianpour et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,125,331 B2 | 2/2012 | Allen et al. |
| 8,160,665 B2 | 4/2012 | Mischler et al. |
| 8,280,476 B2 | 10/2012 | Jina |
| 8,284,046 B2 | 10/2012 | Allen et al. |
| 8,574,165 B2 | 11/2013 | Marsh |
| 8,798,799 B2 | 8/2014 | Deo et al. |
| 9,387,000 B2 | 7/2016 | Corrie et al. |
| 9,551,698 B2 | 1/2017 | Huys et al. |
| 9,737,247 B2 | 8/2017 | Wang et al. |
| 9,743,870 B2 | 8/2017 | Wang et al. |
| 9,933,387 B1 | 4/2018 | McCanna et al. |
| 9,958,409 B2 | 5/2018 | Gerber et al. |
| 10,092,207 B1* | 10/2018 | Windmiller .............. A61N 1/05 |
| 10,136,846 B2 | 11/2018 | Wang et al. |
| 10,231,654 B2 | 3/2019 | Peyser et al. |
| 10,376,188 B2 | 8/2019 | Simpson et al. |
| 10,426,383 B2 | 10/2019 | Huang et al. |
| 10,492,708 B1* | 12/2019 | Windmiller ......... A61M 5/1723 |
| D875,254 S | 2/2020 | Cooke et al. |
| 11,045,142 B1 | 6/2021 | Windmiller et al. |
| 2003/0104119 A1 | 6/2003 | Wilson et al. |
| 2003/0225360 A1 | 12/2003 | Eppstein et al. |
| 2005/0109622 A1 | 5/2005 | Peumans et al. |
| 2006/0015061 A1 | 1/2006 | Kuo et al. |
| 2006/0264716 A1 | 11/2006 | Zander |
| 2007/0170054 A2 | 7/2007 | Wilsey |
| 2007/0213044 A1 | 9/2007 | Steingart et al. |
| 2007/0282246 A1 | 12/2007 | Henley |
| 2008/0097352 A1 | 4/2008 | Beck et al. |
| 2008/0154107 A1 | 6/2008 | Jina |
| 2008/0234562 A1 | 9/2008 | Jina |
| 2009/0069651 A1 | 3/2009 | Zimmermann et al. |
| 2009/0069697 A1 | 3/2009 | Frazier et al. |
| 2009/0088652 A1 | 4/2009 | Tremblay |
| 2009/0131778 A1 | 5/2009 | Jina et al. |
| 2009/0143761 A1 | 6/2009 | Cantor et al. |
| 2009/0259118 A1 | 10/2009 | Feldman et al. |
| 2009/0273358 A1 | 11/2009 | Pampin et al. |
| 2010/0049021 A1 | 2/2010 | Jina et al. |
| 2010/0052897 A1 | 3/2010 | Allen et al. |
| 2010/0056873 A1 | 3/2010 | Allen et al. |
| 2010/0200538 A1 | 8/2010 | Petisce et al. |
| 2010/0286803 A1 | 11/2010 | Tillotson et al. |
| 2011/0087315 A1 | 4/2011 | Richardson-Burns et al. |
| 2011/0105871 A1 | 5/2011 | Zimmermann et al. |
| 2011/0237925 A1 | 9/2011 | Yue et al. |
| 2011/0301677 A1* | 12/2011 | Hendricks .............. A61N 1/056 607/116 |
| 2012/0172692 A1 | 7/2012 | Tamada et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0144131 A1 | 6/2013 | Wang et al. |
| 2013/0225956 A1 | 8/2013 | Huang et al. |
| 2013/0245412 A1 | 9/2013 | Rong et al. |
| 2013/0281808 A1 | 10/2013 | Shieh |
| 2014/0259652 A1 | 9/2014 | Pushpala et al. |
| 2014/0275897 A1 | 9/2014 | Pushpala et al. |
| 2014/0336487 A1 | 11/2014 | Wang et al. |
| 2014/0357964 A1* | 12/2014 | Wisniewski ........... A61B 5/742 600/301 |
| 2015/0276758 A1 | 10/2015 | Addisu |
| 2015/0313527 A1 | 11/2015 | Renlund |
| 2016/0029937 A1 | 2/2016 | Sia et al. |
| 2016/0058342 A1 | 3/2016 | Maiz-Aguinaga et al. |
| 2016/0095541 A1 | 4/2016 | Wang et al. |
| 2016/0270704 A1 | 9/2016 | Deturk |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0007813 A1 | 1/2017 | Negi et al. |
| 2017/0251960 A1 | 9/2017 | Crouther et al. |
| 2018/0116572 A1 | 5/2018 | Simpson et al. |
| 2019/0125223 A1 | 5/2019 | Wang et al. |
| 2019/0224712 A1 | 7/2019 | Petisce et al. |
| 2019/0309433 A1 | 10/2019 | Sattayasamitsathit et al. |
| 2020/0101286 A1 | 4/2020 | Windmiller et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2021/0187286 A1 | 6/2021 | Windmiller et al. |
| 2021/0393201 A1 | 12/2021 | Morelock et al. |
| 2022/0031209 A1 | 2/2022 | Windmiller et al. |
| 2022/0031244 A1 | 2/2022 | Windmiller et al. |

FOREIGN PATENT DOCUMENTS

| | | |
|---|---|---|
| WO | WO-89/006855 A1 | 7/1989 |
| WO | WO-2006/093422 A1 | 9/2006 |
| WO | WO-2009/034313 A2 | 3/2009 |

(56) References Cited

FOREIGN PATENT DOCUMENTS

| WO | WO-2009/034313 A3 | 3/2009 |
|---|---|---|
| WO | WO-2009/064164 A2 | 5/2009 |
| WO | WO-2009/064164 A3 | 5/2009 |
| WO | WO-2010/120364 A2 | 10/2010 |
| WO | WO-2010/120364 A3 | 10/2010 |
| WO | WO-2012/020332 A2 | 2/2012 |
| WO | WO-2012/020332 A3 | 2/2012 |
| WO | WO-2013/058879 A2 | 4/2013 |
| WO | WO-2013/058879 A3 | 4/2013 |
| WO | WO-2015/073459 A1 | 5/2015 |
| WO | WO-2018/164886 A1 | 9/2018 |

OTHER PUBLICATIONS

American Diabetes Association® Press Release (2020). "American Diabetes Association ® Applauds policymakers' Focus on Addressing High Costs of Insulin for Seven Million Americans," 4 pages.
Ammam, M. (2012). "Electrophoretic deposition under modulated electric fields: A review," RSC 140 Advances 2:7633-7646.
Bantle, J.P et al. (1997), "Glucose measurement in patients with diabetes meiiitus with dermal interstitial fluid," J. Lab. Clin. Med. 130:436-441.
Beckles, G.L. et al. (2016). "Disparities in the prevalence of diagnosed diabetes—United States, 1999-2002 and 2011-2014," MMWR 65:1265-1269.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Chou, J.-C et al. (2013). 'Fabrication and Investigation of Arrayed Glucose Biosensor Based on Microfluidic Framework,' IEEE Sensors Journal 13:4180- 4187.
Diabetes Care (2021). "7. Diabetes Technology: Standards of Medical Care in Diabetes—2021," Diabetes Care 44(Supplement 1):S85-S99.
Extended European Search Report dated Feb. 25, 2020, for EP Application No. 17 860 147 884.0, filed Oct. 5, 2017, 7 pages.
Fang, M et al. (2021). "Trends in Diabetes Treatment and Control in U.S. Adults, 1999-2018," N. Engl. Med. 384:2219-2228.
Final Office Action dated Feb. 15, 2022, for U.S. Appl. No. 16/334,022, filed Mar. 17, 2019, 11 pages.
French, D.P et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Grady, M et al. (2017). "Examining the Impact of a Novel Blood Glucose Monitor With Color Range Indicator on Decision-Making in Patients With Type 1 and Type 2 Diabetes and its Association With Patient Numeracy Level," JMIR Diabetes 2:e24.
Grady, M et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
International Search Report dated Jan. 5, 2018, for PCT Application No. PCT/US2017/055314, filed Oct. 5, 2017, 2 pages.
International Search Report dated Feb. 14, 2022, for PCT Application No. PCT/US2021/061903, filed Dec. 3, 2021, 2 pages.
Juvenile Diabetes Research Foundation Continuous Glucose Monitoring Study Group (2008). "Continuous Glucose Monitoring and Intensive Treatment of Type 1 Diabetes." N. Engl. Med. 359:1464-1476.
Karter, A.J. et al. (2021). "Association of Real-time Continuous Glucose Monitoring With Glycemic Control and Acute Metabolic Events Among Patients With Insulin-Treated Diabetes," JAMA 325:2273-2284.
Kassim, A. et al., (2001), "Effect of reactor configuration and temperature on Electropolymerization of Sodium Camphorsulfonate-Doped Polypyrrole," Malaysian Journal of Analytical Sciences 7:25-27.
Mangold, K.M. (2001), "Reference electrodes based on conducting polymer bilayers," Synthetic Metals 119:345-346.
Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.
McClatchey, P.M. et al. (2019). "Fibrotic Encapsulation is the Dominant Source of Continuous Glucose Monitor Delays," Diabetes 68:1892-1901.
Neerken, S. et al. (2004). "Characterization of age-related effects in human skin: A comparative study that applies confocal laser scanning microscopy and optical coherence tomography," J. Biomed. Optics 9:274-281.
Non-Final Office Action dated Apr. 16, 2019, for U.S. Appl. No. 16/152,3/2, filed Oct. 4, 2018, 11 pages.
Non-Final Office Action dated Jul. 1, 2021, for U.S. Appl. No. 16/334,022, filed Mar. 17, 2019, 11 pages.
Notice of Allowance dated Aug. 28, 2018, for U.S. Appl. No. 15/590,105, filed May 9, 2017, 8 pages.
Notice of Allowance dated Sep. 9, 2019, for U.S. Appl. No. 16/152/372, filed Oct. 4, 2018, 7 pages.
Polonsky, W.H. et al. (2011). "A survey of blood glucose monitoring in patients with type 2 diabetes; Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Waltman, R.J. et al. (1986). "Electrically conducting polymers: a review of the eiectropolymerization reaction, of the effects of chemical structure on polymer film properties, and of applications towards technology," Canadian Journal of Chemistry 64:76-95.
Written Opinion of the International Searching Authority dated Jan. 5, 2018, for PCT Application No. PCT/US2017/055314, filed Oct. 5, 2017, 9 pages.
Written Opinion of the International Searching Authority dated Feb. 14, 2022, for PCT Application No. PCT/US2021/061903, filed Dec. 3, 2021, 9 pages.

* cited by examiner

TISSUE-PENETRATING ELECTROCHEMICAL SENSOR FEATURING A CO-ELECTRODEPOSITED THIN FILM COMPRISED OF POLYMER AND BIO-RECOGNITION ELEMENT

CROSS REFERENCE TO RELATED APPLICATION

The Present application is a continuation application of U.S. patent application Ser. No. 16/152,372, filed on Oct. 4, 2018, which is a continuation application of U.S. patent application Ser. No. 15/590,105, filed on May 9, 2017, now U.S. patent Ser. No. 10/092,207, issued on Oct. 9, 2018, which claims priority to U.S. Provisional Patent Application No. 62/336,724, filed on May 15, 2016, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to electrochemical sensors.

Description of the Related Art

Electrochemical sensor devices have witnessed increased development activity in recent years, driven primarily by the challenge of in vivo glucose sensing. However, to date, these devices are manufactured using labor- and time-consuming physical assembly processes, especially to impart their selective chemical sensing capabilities. In this vein, such devices have not leveraged high-volume automated manufacturing processes to fabricate electrochemical sensors with high yield and uniformity.

The prior art discusses various sensors.

Meyer et al., U.S. Pat. No. 4,756,807 for a Chemically modified electrodes for the catalytic reduction of CO2 discloses an electrode that has a film adsorbed to its surface by reductive electropolymerization of (vbpy)Re(CO)3 Cl (4-vinyl-4'-methyl-2,2'-bipyridine tricarbonylchlororhenium(I)) or its acetonitrile analogue, [(vbpy)Re(CO)3 (MeCN)]+(4-vinyl-4'-methyl-2,2'-bipyridine tricarbonylacetonitrile rhenium (I)). The poly(vbpy)Re(CO)3 Cl or poly [(vbpy)Re(CO)3 (MeCN)]+ adsorbed onto the electrode, acts as a catalyst for CO2 reduction to CO. Stability and the reactivity of the polymer film may be increased by co-reductive electropolymerization of either of the aforesaid Re complexes with [(bpy)2 Ru(vpy)2 2+(bis(4-vinyl-pyridine) bis(2,2'-bipyridine) ruthenium (II)) (vpy is 4-vinylpyridine). A bilayer film assembly consisting of poly-[(bpy)2 Ru(vpy) 2]2+ as an inner film and the aforementioned copolymer of Ru/Re yields even greater reactivity to CO2; a method of forming a polymeric film on an electrode; and a method of reducing CO2 to CO using an electrode having a polymeric film adsorbed to its surface.

Yacynych, U.S. Pat. No. 5,540,828 for a Method for making electrochemical sensors and biosensors having a polymer modified surface discloses a method for making a sensing element for use in a sensor or biosensor that amperometrically measures the concentration of an analyte in a liquid, includes the following sequential steps: a) obtaining an electrode; b) immersing the electrode in a solution of monomer that is capable of being electropolymerized into an electrically insulating polymer; c) flowing an electric current from a cathode through the solution to the electrode at a voltage and amperage sufficient to cause the monomer to polymerize on the surface of the electrode, thereby yielding an electrode coated with an adherent layer of electrically insulating polymer; and e) impregnating the polymeric coating on the surface with a sensing agent that is capable, when contacted by a specific analyte in a chemical or biological liquid, of generating an electroactive molecule that can be detected amperometrically.

Yacynych et al, U.S. Pat. No. 5,286,364 for a Surface-modified electochemical biosensor discloses a biosensor.

Wilson et al., U.S. Pat. No. 6,814,845 for a Method for depositing an enzyme on an electrically conductive substrate discloses improved biosensors are provided having excellent selectivity and stability properties, together with methods of preparing the biosensors. A preferred biosensor includes an electrode having enzyme deposited thereon together with a layer of electropolymerized polymer intermingled with the enzyme; a crosslinked silane film is applied over the polymer layer, and a final coating of polyurethane is formed over the film. In preparative procedures, the enzyme is electrodeposited using an aqueous enzyme solution containing a nonionic surfactant at a concentration level preferably in excess of the critical micelle concentration of the surfactant. In the case of a glucose sensor, the polymer layer is preferably polyphenol, while the silane film is crosslinked (3-aminopropyl) trimethoxysilane. The preferred biosensors have greatly enhanced selectivity stabilities.

Haesik et al., U.S. Pat. No. 6,413,396 for an Enzyme electrode sensor and manufacturing method thereof discloses an enzyme electrode sensor and a fabricating method thereof, and more particularly, an enzyme electrode sensor which is a biosensor using electrochemical measurement and a manufacturing method thereof. The sensor includes an electrode, a first nonconducting polymer layer formed by electropolymerization outside the electrode wherein enzyme is immobilized in the nonconducting polymer layer, a second nonconducting polymer layer in which enzyme is not immobilized, the second nonconducting layer formed by electropolymerization outside the first nonconducting polymer layer, and an outer layer formed outside the second nonconducting layer. The sensor selectivity is improved as the interference of organic materials is inhibited, and the interference of acetaminophen causing the major problem with a glucose sensor is controlled effectively by the sensor.

Tissue-penetrating electrochemical sensors represent a promising avenue towards the minimally-invasive quantification of a number of relevant analytes in the physiological fluid, such as interstitial fluid, blood, serum, and plasma. Currently, to impart the ability to selectively quantify chemical/biochemical analytes of interest, membranes comprising of one or more polymers with a biorecognition element dispersed therein are cast in a manual fashion, keeping costs high and sensor-to-sensor uniformity low. In this application, tissue can refer to, but is not limited to, skin, organs, and cells.

Prior art solutions have been concerned with the immobilization of biorecognition elements by means of entrapment in a polymeric membrane cast by a manual, human-operated process (via dip or drop casting in an aqueous- or solvent-based solution of polymer and enzyme) or by means of the assistance of an automated liquid reagent dispensing robot. This is a serialized process and, as a consequence, low throughput and high device cost are challenges that still confront skin- and tissue-penetrating electrochemical sensor production. When performed by a human operator, such deposition processes often result in a sensor response characterized by a wide degree of variance and hence sensors for clinical applications must often undergo quality control or calibration measures on an individual basis, thereby further impeding the transition to mass production techniques.

BRIEF SUMMARY OF THE INVENTION

The technology disclosed herein addresses the above challenges by disclosing a method for the automated and parallelized co-deposition of a conducting polymer and biorecognition element at one or more working electrodes of a tissue-penetrating electrochemical sensor.

The present invention provides for a method to impart the ability to selectively quantify chemical/biochemical analytes occupying physiological fluids via an automated process that allow the precise and spatially-defined simultaneous deposition of a thin-film of polymer containing an immobilized biorecognition element dispersed therein.

The technology described herein also involves a method for automated, volume-scale functionalization of a tissue-penetrating electrochemical sensor to yield selective chemical or biochemical recognition capability in vivo.

The present invention delineates a method for the simultaneous co-deposition of both an entrapment polymer and an immobilized biorecognition element onto at least one working electrode using an electro-deposition process for skin- and tissue-penetrating electrochemical sensor functionalization that is highly amenable to high-throughput, automated, parallelized, and highly reproducible manufacturing methods that do away with the need for a human operator during the sensor functionalization process. Indeed, with the trend towards increasing sensor miniaturization, conventional manual processes associated with sensor functionalization to impart a selective biorecognition capability is becoming increasingly inaccessible using a human operator and the need remains for a sensor functionalization strategy that can be exploited along conventional precision manufacturing lines, such as those used for the medical device, MEMS, and semiconductor industries.

One aspect of the present invention is a tissue-penetrating electrochemical sensor device for the quantification of a chemical or biochemical entity in a physiological fluid. The device comprises a tissue-penetrating electrochemical sensor comprising at least one spatially-defined working electrode, and a conducting polymer film comprising an organic electroactive monomer precursor and at least one biorecognition element. The organic electroactive monomer precursor and the at least one biorecognition element dispersed uniformly and physically entrapped in the conducting polymer film. The conducting polymer film is produced by immersing the tissue-penetrating electrochemical sensor in a solution containing the at least one biomolecular recognition element and the organic electroactive monomer precursor which is dissolved in the solution, and wherein application of an oxidizing potential or a reducing potential at the spatially-defined working electrode causes the co-electrodeposition of the conducting polymer film.

Another aspect of the present invention is a method for the fabrication of a tissue-penetrating electrochemical sensor for the quantification of a chemical or biochemical entity in a physiological fluid. The method includes immersing a tissue-penetrating electrochemical sensor comprising at least one spatially-defined working electrode in a solution comprising at least one biomolecular recognition element and an organic electroactive monomer precursor dissolved in the solution. The method also includes applying of an oxidizing potential or a reducing potential at the spatially-defined working electrode, causing a co-electrodeposition of a polymer film from the organic electroactive monomer precursor and the at least one biorecognition element dispersed uniformly and physically entrapped in the polymer film.

The organic electroactive monomer precursor is preferably selected for at least one of its perm-selective properties following conversion to a thin-film of polymer, its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, or its self-limited growth during conversion to a thin-film of polymer.

The biomolecular recognition element comprises at least one of an enzyme, biocatalyst, inorganic catalyst, ion-selective material, antibody, oligonucleotide, electrochemical redox mediator, cell, or organelle.

The tissue-penetrating electrochemical sensor further comprises at least a reference electrode or a counter electrode.

The oxidizing potential or reducing potential is either a fixed potential or a time-varying potential.

The oxidizing potential or reducing potential is applied using one of an amperometric technique, a voltammetric technique, a conductometric technique, or a coulometric technique.

The oxidizing potential or the reducing potential is selected to result in the formation of a precise thickness of the conducting polymer film.

The oxidizing potential or the reducing potential is applied for a specified time duration to result in the formation of a precise thickness of the conducting polymer film.

The oxidizing potential or the reducing potential is selected to pass a specified amount of charge through at least one of the working electrode to result in the formation of a precise thickness of the conducting polymer film.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
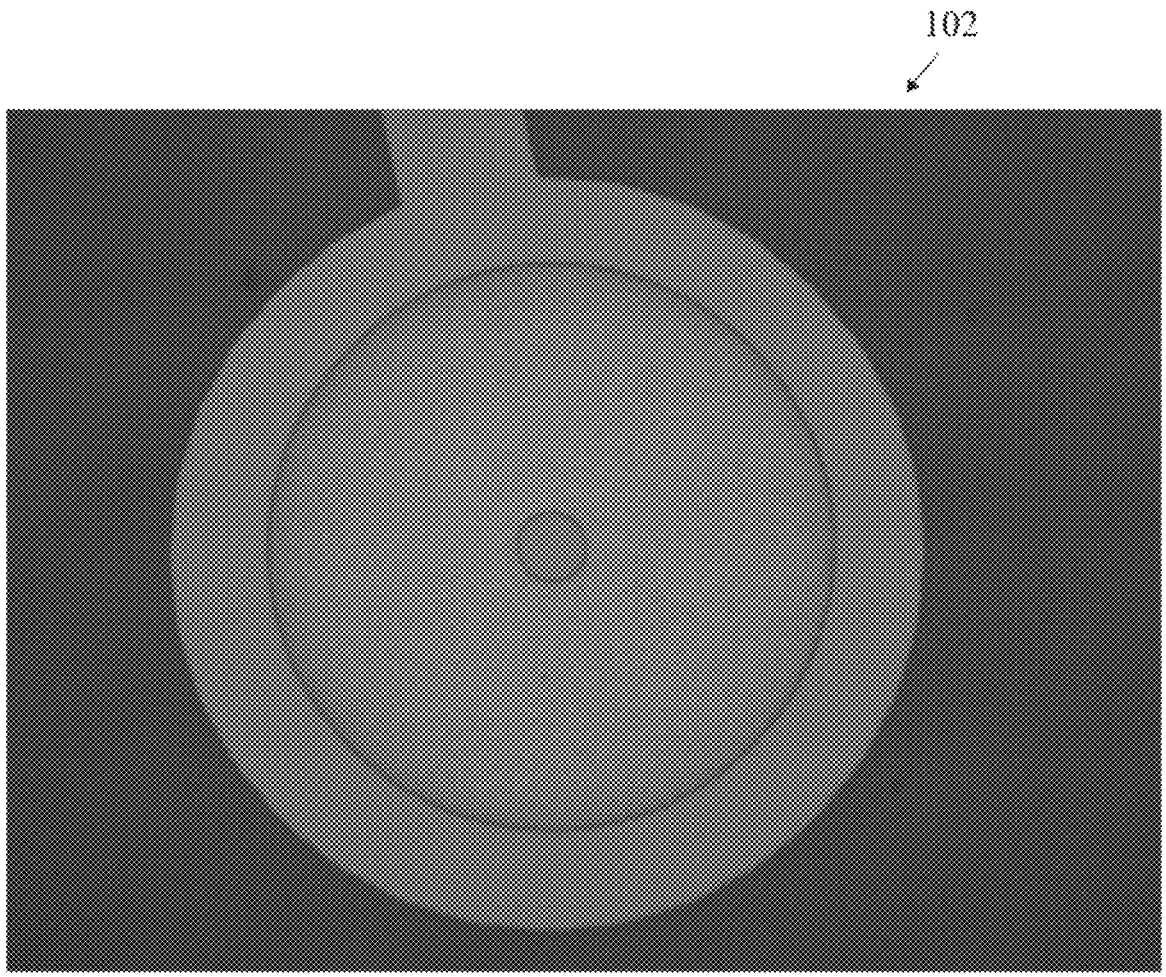
FIG. 1 is an optical micrograph of an unfunctionalized working electrode.

One embodiment is a tissue-penetrating electrochemical sensor device for the quantification of a chemical or biochemical entity in a physiological fluid. The device preferably comprises a tissue-penetrating electrochemical sensor comprising at least one spatially-defined working electrode, and a conducting polymer film comprising an organic electroactive monomer precursor and at least one biorecognition element. The organic electroactive monomer precursor and the at least one biorecognition element dispersed uniformly and physically entrapped in the conducting polymer film. The conducting polymer film is produced by immersing the tissue-penetrating electrochemical sensor in a solution containing the at least one biomolecular recognition element and the organic electroactive monomer precursor which is dissolved in the solution, and wherein application of an oxidizing potential or a reducing potential at the spatially-defined working electrode causes the co-electrodeposition of the conducting polymer film.

Another embodiment is a method for the fabrication of a tissue-penetrating electrochemical sensor for the quantification of a chemical or biochemical entity in a physiological fluid. The method includes immersing a tissue-penetrating electrochemical sensor comprising at least one spatially-defined working electrode in a solution comprising at least one biomolecular recognition element and an organic electroactive monomer precursor dissolved in the solution. The method also includes applying of an oxidizing potential or a reducing potential at the spatially-defined working electrode, causing a co-electrodeposition of a polymer film from the organic electroactive monomer precursor and the at least one biorecognition element dispersed uniformly and physically entrapped in the polymer film.

The method provides for reliably dispensing a reagent containing at least one biorecognition at the micron-scale, as required to functionalize microelectrodes and microelectrode arrays. The method provides the formation of a polymeric film containing a biorecognition element by means of electro-polymerization enables the precise control of the thickness of the layer as well as the formation of a very thin layer. Past conventional methods of forming a polymeric layer by use of drop casting, dip coating, spin coating, or dispensing had the difficulty of controlling the thickness of the layer, thereby forming a relatively thick and non-uniform layer. Therefore, electro-polymerization utilized in the present invention is very effective for the reproducible formation of a layer as well as the simultaneous realization of co-deposition of both the polymer and the biorecognition element.

In addition to variations in film thickness caused by conventional sensor functionalization approaches, these techniques require multiple steps to create a selective, diffusion-limiting, interference-rejecting sensor membrane and it is the case that a polymeric film is cast on the electrode following a prior biorecognition element deposition step, which further contributes to decreased sensor uniformity and increased manufacturing cost and time. The simultaneous co-deposition of both the polymer and the biorecognition element, as disclosed in the current invention, serve to mitigate these challenges that have plagued the electrochemical sensor industry for some time.

Precisely-defined thin-films, whose thickness and porosity can be precisely controlled by the suitable application of voltage, current, or charge that is passed through the electrode, also embody the advantage that the approach requires minimal quantity of reagent, thereby contributing to a reduction in cost to manufacture.

The technology disclosed herein discloses a method for the automated and parallelized co-deposition of a conducting polymer and biorecognition element at one or more working electrodes of a tissue-penetrating electrochemical sensor. The method involves the immersion of the electrochemical sensor in a solution of an organic electroactive monomeric precursor (to the conducting polymer) and biorecognition element (enzyme, antibody, etc.) and applying a fixed- or time-varying potential at one or more of the working electrodes to instigate co-electrodeposition. This encourages the electro-polymerization of a conducting polymer film, synthesized from the monomeric precursor, onto the working electrode surface. Because it is uniformly dispersed in solution and often is a large molecule (larger than the pore size of the polymer), the biorecognition element is also entrapped, in a spatially uniform fashion, in the polymer film and can, optionally, serve as the counter-ion or dopant during the electro-polymerization process through suitable choice of a biorecognition element with appropriate isoelectric point and solution pH.

Leveraging this self-assembly process, which is also self-limiting, the thickness and porosity of the polymeric film is adjusted via modification of the applied potential, current, or charge passed through the electrochemical cell during the co-electrodeposition process. This has wide-ranging implications pertaining to the sensitivity, selectivity, stability, and response time of the as-synthesized tissue-penetrating electrochemical sensor.

The disclosed technique facilitates spatially-defined deposition of precisely-controlled thin-films on one or more working electrode surfaces and allows the sensor designer to synthesize entrapment membranes to achieve certain utilitarian features such as co-circulating electroactive interference rejection (via perm- or charge-selectivity), increased linearity, extended lifetime, minimal signal drift, or reduced tendency to undergo biofouling when used in vivo.

Simple and reproducible formations of chemically- and biochemically-selective polymer films can be formed with the disclosed method, which obviates the need for multiple biorecognition element casting and polymer casting steps by allowing for the simultaneous co-deposition of a thin-film containing both an entrapping polymer and biorecognition element. As such, the as-disclosed sensor functionalization strategy enables parallelized sensor functionalization without human intervention and is amenable to implementation along assembly lines or semiconductor fabrication processes.

The following commercially-available components are used in the synthesis of the sensor:

The voltage/current source is preferably a CH INSTRUMENTS Model 10000 Series Multi-Potentiostat, Metrohm Autolab PGSTAT Series Potentiostat Galvanostat, or Palmsens EmStat Potentiostat. The voltages utilized depend on the film, and generally range from −0.2 volts to +1.0 volts. The current transduced ranges from 10 picoAmperes (pA) to 100 microAmperes (μA), and is dependent on whether a singular electrode is electro-deposited or if multiple electrodes are electro-deposited as a group.

The working electrode is preferably a CH INSTRUMENTS CHI101 2 mm-diameter gold disc microelectrode, or a METROHM MF-2150 100 μm-diameter platinum disc microelectrode.

The tissue-penetrating electrochemical sensor is preferably a subcutaneous, percutaneous, transdermal, or intradermal sensor in which an electrical stimulus is applied to encourage a redox reaction and in which a voltage, current, charge, resistance, or impedance property is measured to infer the concentration of a particular chemical/biochemical analyte of interest present in the physiological fluid compartment in which the sensor is located. The sensor also comprises at least one working electrode (defined below) and at least one of a counter electrode and a reference electrode.

The working electrode is preferably a spatially-defined electrode whereby the electrochemical sensing operation is to occur; functionalized with a polymer and biorecognition element to impart the selective ability to transduce the chemical/biochemical of interest into an electrical signal. A defined voltage, current, or amount of charge is applied as a stimulus to the working electrode to instigate a redox reaction and a voltage, current, charge, resistance, or impedance response is measured to infer the concentration of a particular chemical/biochemical analyte of interest.

The organic electroactive monomer precursor is preferably an organic monomer that is either oxidized or reduced by the application of a suitable voltage, current, or amount of charge on a working electrode surface and concomitantly electro-deposited/electro-polymerized on the working electrode surface from a solution in which it is dissolved.

The biorecognition element is preferably an organic, inorganic, or biological compound that selectively binds, catalyzes, or sieves a particular chemical/biochemical analyte of interest and, in doing so, changes its electrical properties (voltage, current, charge, resistance, or impedance) or produces an electroactive product ($H_2O_2$, NADH, etc.). Examples of a biorecognition element include, but are not limited to, an enzyme, biocatalyst, inorganic catalyst, ion-selective material, antibody, oligonucleotide, electrochemical redox mediator, cell, or organelle.

The conducting polymer is preferably synthesized from the organic electroactive monomer precursor through the process of electro-polymerization. The conducting polymer serves to physically entrap the biorecognition element in its highly porous matrix, thereby forming a thin-film with selective sensing capabilities. Alternatively, the biorecognition element can serve as the dopant or counter-ion through the appropriate selection of the biorecognition element's isoelectric point and solution pH in which the organic electroactive monomer precursor and biorecognition element are dissolved. The polymer can also be selected to exhibit perm-selective, charge-selective, size-selective, or anti-biofouling properties. The polymer film thickness preferably ranges from 5 nanometers ("nm") to 50 nm. The thickness is primarily governed by the voltage applied, the time that the voltage is applied, the amount of the monomeric precursor in the solution, and the geometry of the electrode. The porosity of the film and the perm-selectivity of the film are also adjusted by these factors.

The voltage or current source is either a power supply, potentiostat, galvanostat, function generator, or any source of electrical voltage or current. The voltage or current source is operated to apply a particular voltage, current, or amount of charge. The voltage or current source is terminated once a certain amount of time has transpired or charge has passed through the working electrode. The voltages utilized depend on the film and generally range from −0.2 volts to +1.0 volts. The current transduced ranges from 10 picoAmperes (pA) to 100 microAmperes (μA), and is dependent on whether a singular electrode is electro-deposited or if multiple electrodes are electro-deposited as a group.

The solution composition comprises the organic electroactive monomeric precursor dissolved in $H_2O$ and optionally salt(s) from the group consisting of NaCl, KCl, $MgSO_4$, $CaCl_2$, $Na_2HPO_4$, $NaH_2PO_4$, $K_2HPO_4$, and $KH_2PO_4$. The organic monomeric precursor is preferably one or more of, but not limited to, the following: aniline, pyrrole, acetylene, phenylene, phenylene vinylene, phenylene diamine, thiophene, 3,4-ethylenedioxythiophene, aminophenylboronic acid.

The method steps of the invention include the following:
1) Immersion of a tissue-penetrating electrochemical sensor in a solution of at least one of a biorecognition element and an organic electroactive monomer precursor. A tissue-penetrating electrochemical sensor 100 containing, in this example, exactly one counter electrode 101, one working electrode 102, and one reference electrode 103 is immersed in a solution 104 comprising at least one of a biomolecular recognition element and at least one of an organic electroactive monomer precursor dissolved in said solution. In a two-electrode embodiment, a tissue-penetrating electrochemical sensor 100 containing, in this example, exactly one working electrode 102 and one reference electrode 103 is immersed in a solution 104 comprising at least one of a biomolecular recognition element and at least one of an organic electroactive monomer precursor dissolved in said solution. 2) Application of an oxidizing or reducing potential upon at least one working electrode contained in electrochemical sensor. A voltage or current source 105 is connected, in an ohmic fashion, to counter electrode 101 and at least one of 102 and 103; a constant or time-varying potential is applied to counter electrode 101 to pass a controlled and pre-determined amount of current or charge through counter electrode 101. 3) Simultaneous co-electrodeposition of a thin-film of polymer comprised of organic electroactive monomer precursor and the at least one biorecognition element. Following the application of a potential, current, or charge, the formation of a thin-film, typically on the order of 1-100 nm, of the polymerized organic electroactive monomer, serves to entrap the biomolecular recognition element in the highly porous matrix created therein. This processes functionalizes the working electrode 102 of the tissue-penetrating electrochemical sensor and allows it to achieve the selective quantification of at least one chemical or biochemical analyte in a physiological fluid.

The inputs of the invention are as follow:
1) an organic electroactive monomer precursor. The organic monomer is either oxidized or reduced by the application of a suitable voltage, current, or amount of charge on a working electrode surface and concomitantly electro-deposited/electro-polymerized on the working electrode surface from a solution in which it is dissolved.

2) Biorecognition element. An organic, inorganic, or biological compound that selectively binds, catalyzes, or sieves a particular chemical/biochemical analyte of interest and, in doing so, changes its electrical properties (voltage, current, charge, resistance, or impedance) or produces an electroactive product ($H_2O_2$, NADH, etc.). Examples of a biorecognition element include, but are not limited to, an enzyme, biocatalyst, inorganic catalyst, ion-selective material, antibody, oligonucleotide, electrochemical redox mediator, cell, or organelle.

3) Electrical stimulus. A specified and controlled voltage, current, or amount of charge is applied. The electrical stimulus is terminated once a certain amount of time has transpired or charge has passed through the system.

The outputs of the invention are as follows: Functionalized working electrode. One or more working electrodes are coated with a thin-film, typically on the order of 1-100 nm, of the polymerized organic electroactive monomer 110, which serves to entrap the biomolecular recognition element to form a co-deposited, highly porous polymer-biorecognition element matrix 109. This processes functionalizes the working electrode 102 of the tissue-penetrating electrochemical sensor and allows it to achieve the selective quantification of at least one chemical or biochemical analyte in a physiological fluid.

FIG. 1 is an optical micrograph of an unfunctionalized working electrode.

Figure 2:
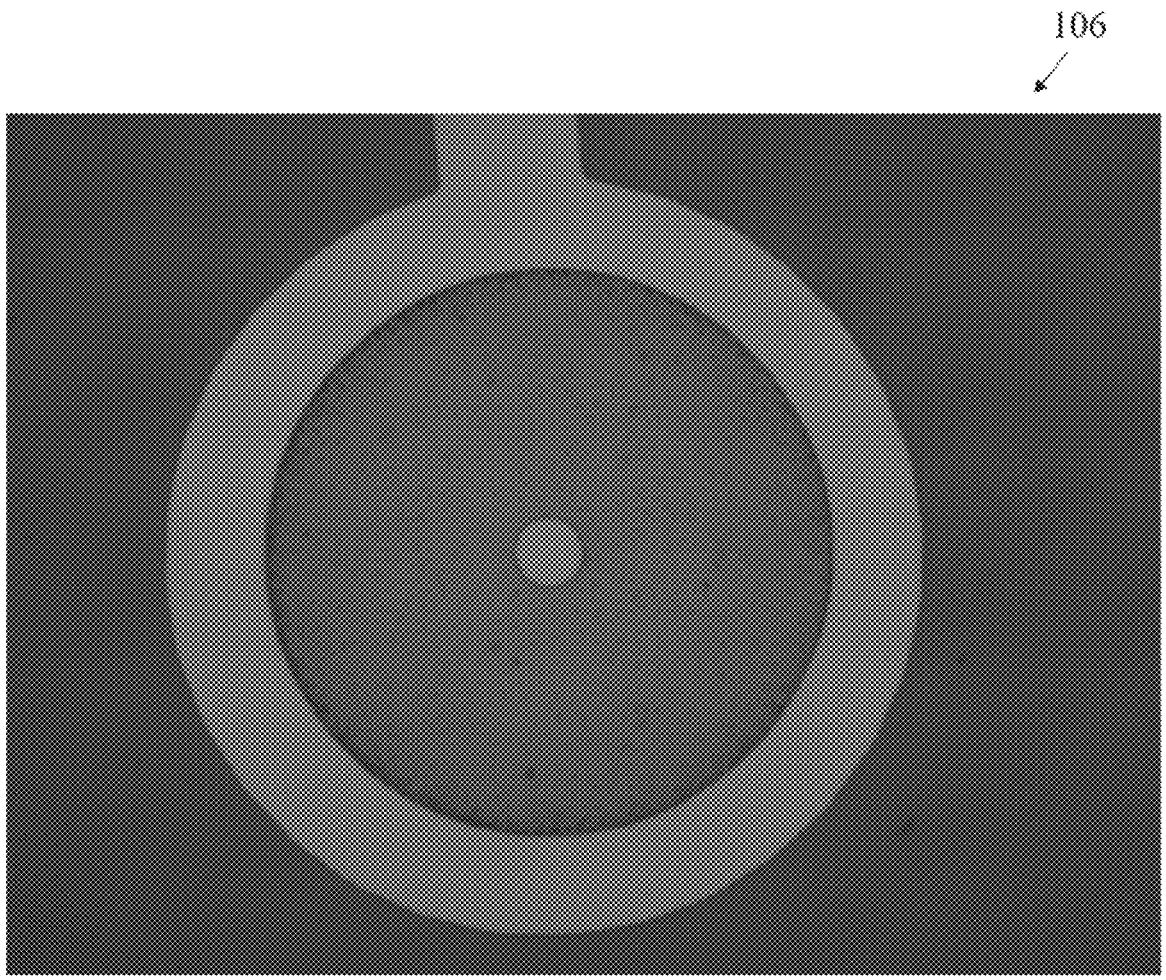
FIG. 2 is an optical micrograph of the working electrode shown in FIG. 1 following functionalization.

FIG. 2 is an optical micrograph of the working electrode shown in FIG. 1 following functionalization. The presence of a thin-film of co-electrodeposited polymer and enzyme can be observed from the image.

Figure 3:
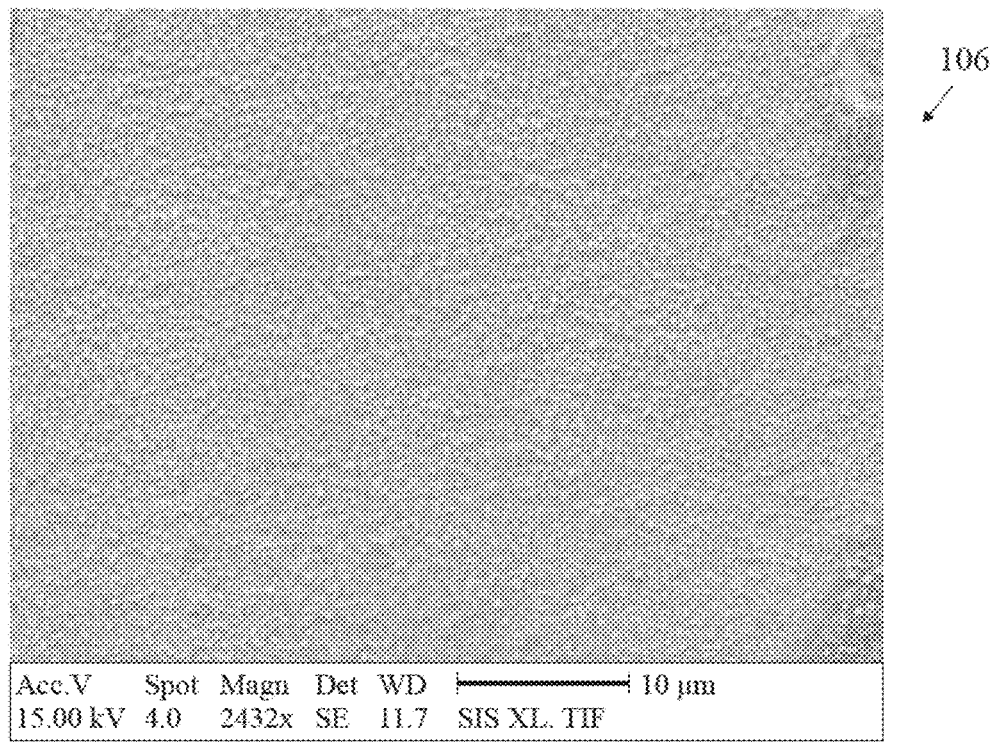
FIG. 3 is an electron micrograph delineating the surface morphology of the functionalized working electrode provided in FIG. 2.

FIG. 3 is an electron micrograph delineating the surface morphology of the functionalized working electrode provided in FIG. 2.

Figure 4:
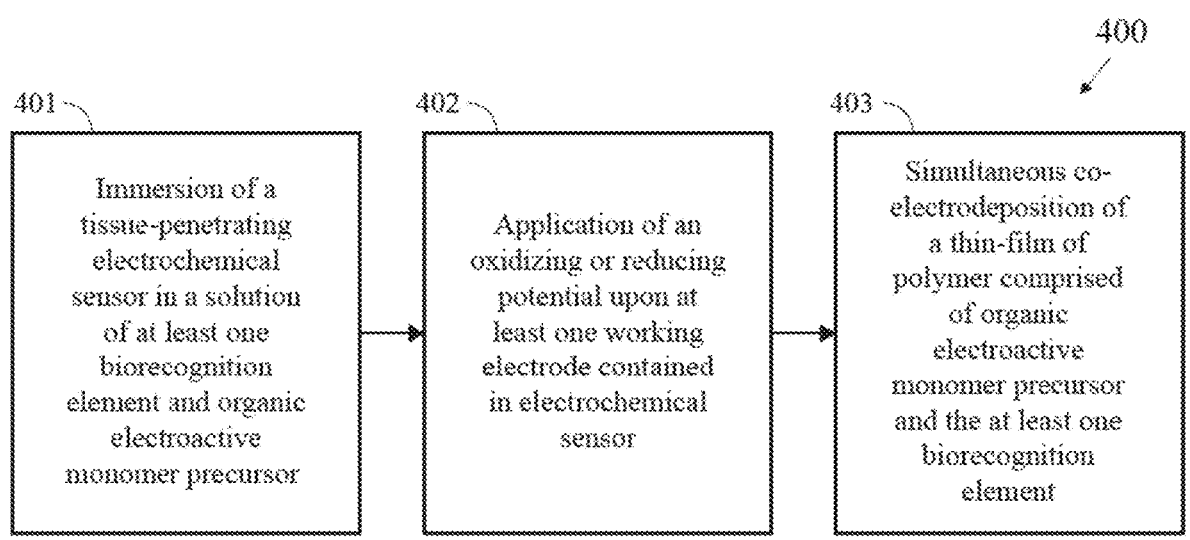
FIG. 4 is a block/process flow diagram illustrating the major constituents involved in the functionalization of a tissue- or skin-penetrating electrochemical sensor to facilitate chemical or biochemical quantification of various analytes in physiological fluids.

FIG. 4 is a block/process flow diagram illustrating the major constituents involved in the functionalization of a tissue- or skin-penetrating electrochemical sensor to facilitate chemical or biochemical quantification of various analytes in physiological fluids.

Figure 5:
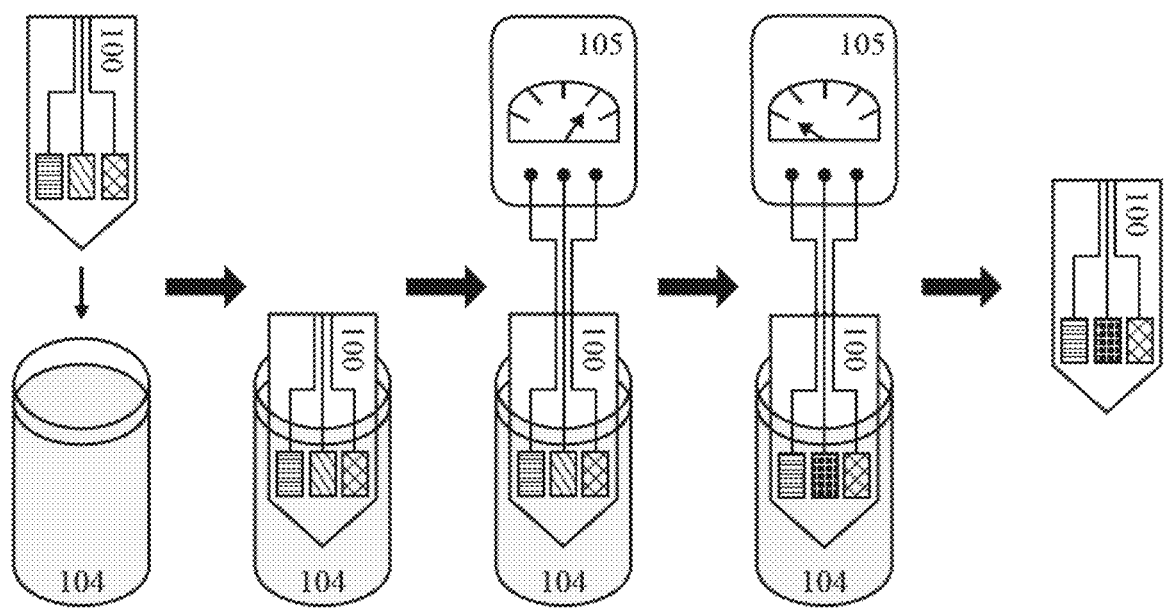
FIG. 5 is a schematic illustration delineating the major steps involved in the co-electrodeposition of a polymer-biorecognition element film on at least one working electrode of a tissue-penetrating three-electrode electrochemical sensor.

FIG. 5 is a schematic illustration delineating the major steps involved in the co-electrodeposition of a polymer-biorecognition element film on at least one working electrode of a tissue-penetrating three-electrode electrochemical sensor. Briefly, a tissue-penetrating electrochemical sensor 100 containing, in this example, exactly one counter electrode 101, one working electrode 102, and one reference electrode 103 is immersed in a solution 104 comprising at least one of a biomolecular recognition element and at least one of an organic electroactive monomer precursor dissolved in said solution. A voltage or current source 105 is connected, in an ohmic fashion, to 102 and at least one of 101 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 6:
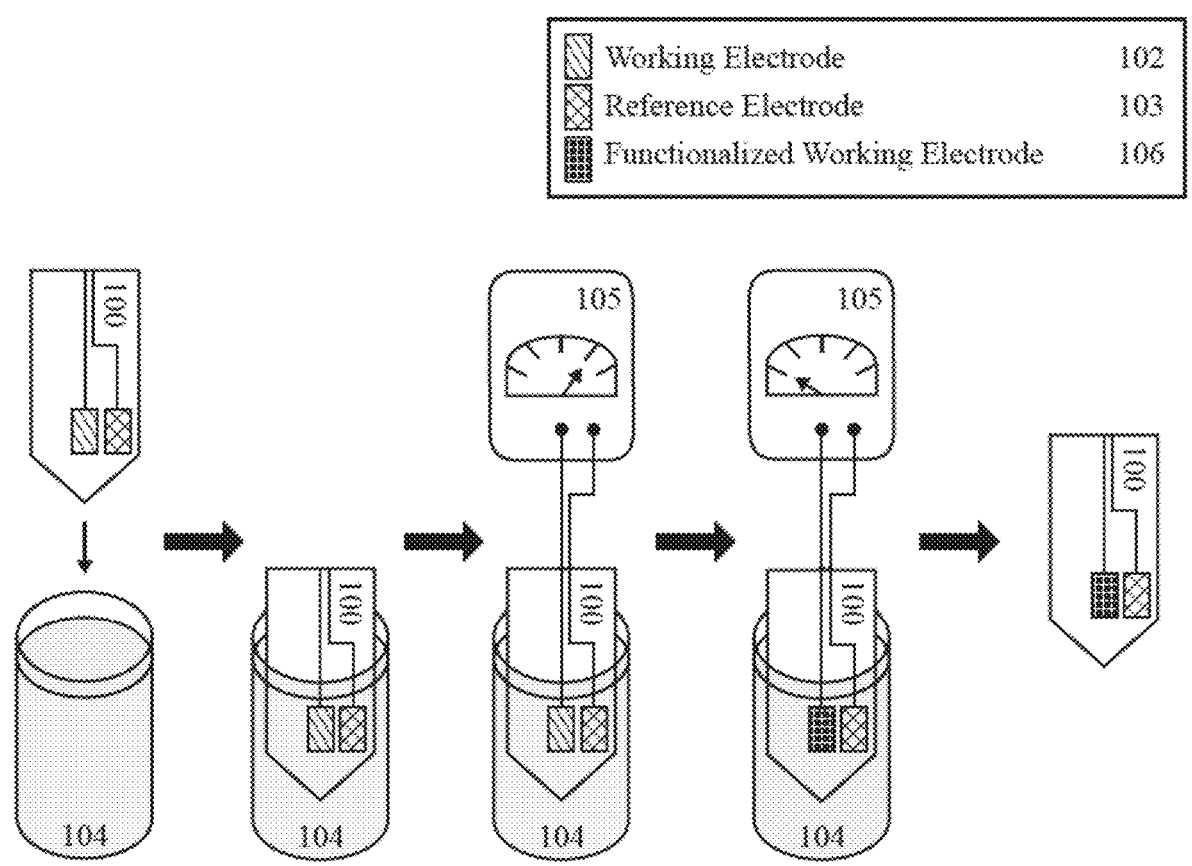
FIG. 6 is a schematic illustration delineating the major steps involved in the co-electrodeposition of a polymer-biorecognition element film on at least one working electrode of a tissue-penetrating two-electrode electrochemical sensor.

FIG. 6 is a schematic illustration delineating the major steps involved in the co-electrodeposition of a polymer-biorecognition element film on at least one working electrode of a tissue-penetrating two-electrode electrochemical sensor. Briefly, a tissue-penetrating electrochemical sensor 100 containing, in this example, exactly one working electrode 102 and one reference electrode 103 is immersed in a solution 104 comprising at least one of a biomolecular recognition element and at least one of an organic electroactive monomer precursor dissolved in said solution. A voltage or current source 105 is connected, in an ohmic fashion, to 102 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 7:
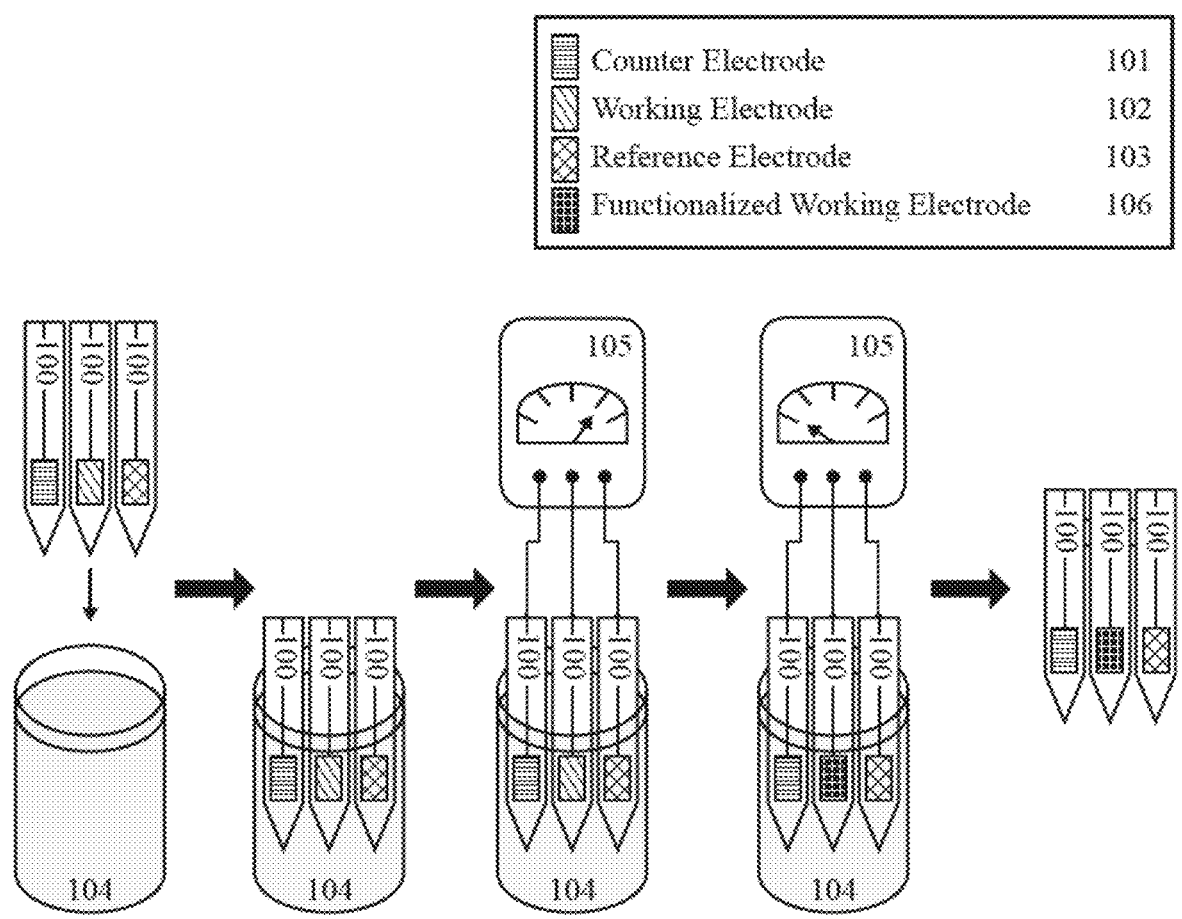
FIG. 7 is a schematic illustration delineating the major steps involved in the co-electrodeposition of a polymer-biorecognition element film on at least one working electrode of a multi-component tissue-penetrating three-electrode electrochemical sensor, whereby each electrode is located within an isolated tissue-penetration electrochemical sensor.

FIG. 7 is a schematic illustration delineating the major steps involved in the co-electrodeposition of a polymer-biorecognition element film on at least one working electrode of a multi-component tissue-penetrating three-electrode electrochemical sensor, whereby each electrode is located within an isolated tissue-penetration electrochemical sensor. Briefly, three tissue-penetrating electrochemical sensors 100 containing, in this example, exactly one counter electrode 101, one working electrode 102, and one reference electrode 103 are immersed in a solution 104 comprising at least one of a biomolecular recognition element and at least one of an organic electroactive monomer precursor dissolved in said solution. A voltage or current source 105 is connected, in an ohmic fashion, to 102 and at least one of 101 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 8:
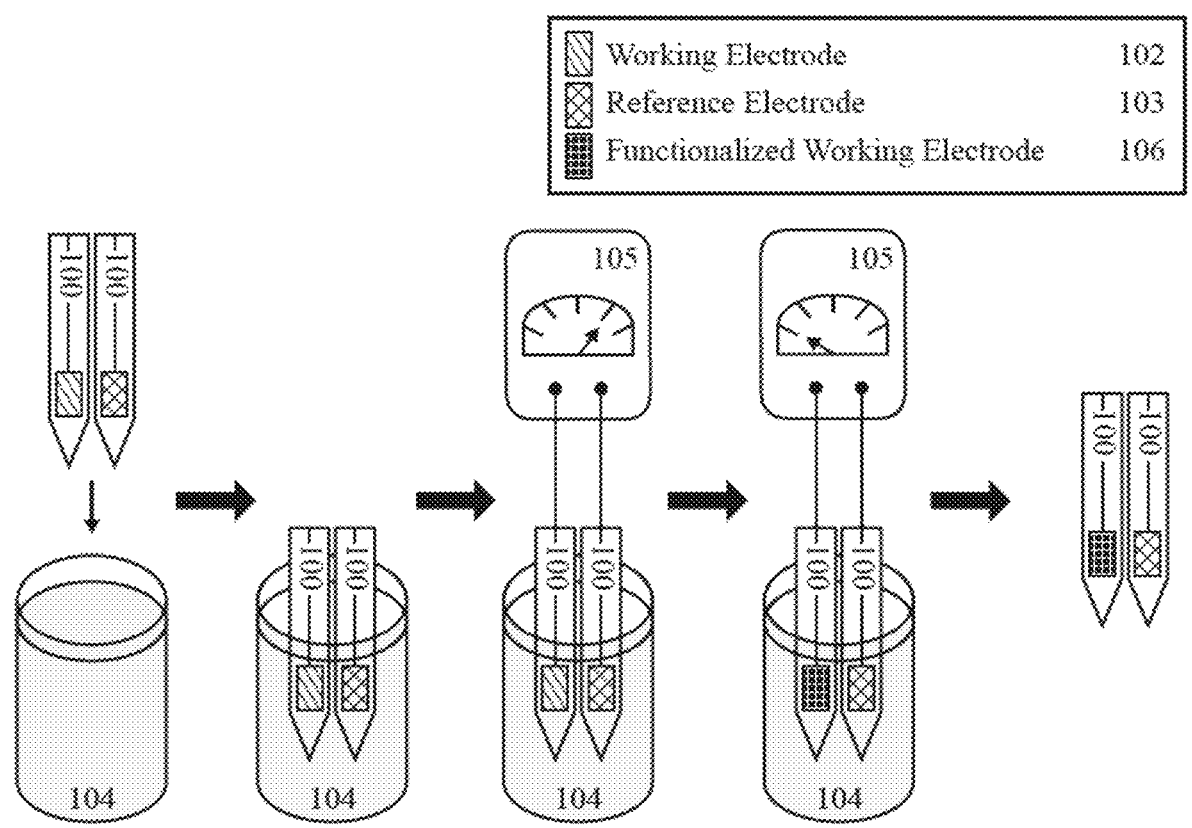
FIG. 8 is a schematic illustration delineating the major steps involved in the co-electrodeposition of a polymer-biorecognition element film on at least one working electrode of a tissue-penetrating two-electrode electrochemical sensor.

FIG. 8 is a schematic illustration delineating the major steps involved in the co-electrodeposition of a polymer-biorecognition element film on at least one working electrode of a tissue-penetrating two-electrode electrochemical sensor. Briefly, two tissue-penetrating electrochemical sensors 100 containing, in this example, exactly one working electrode 102 and one reference electrode 103 are immersed in a solution 104 comprising at least one of a biomolecular recognition element and at least one of an organic electroactive monomer precursor dissolved in said solution. A voltage or current source 105 is connected, in an ohmic fashion, to working electrode 102 and reference electrode 103; a constant or time-varying potential is applied to working electrode 102 to pass a controlled and pre-determined amount of current or charge through working electrode 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 9:
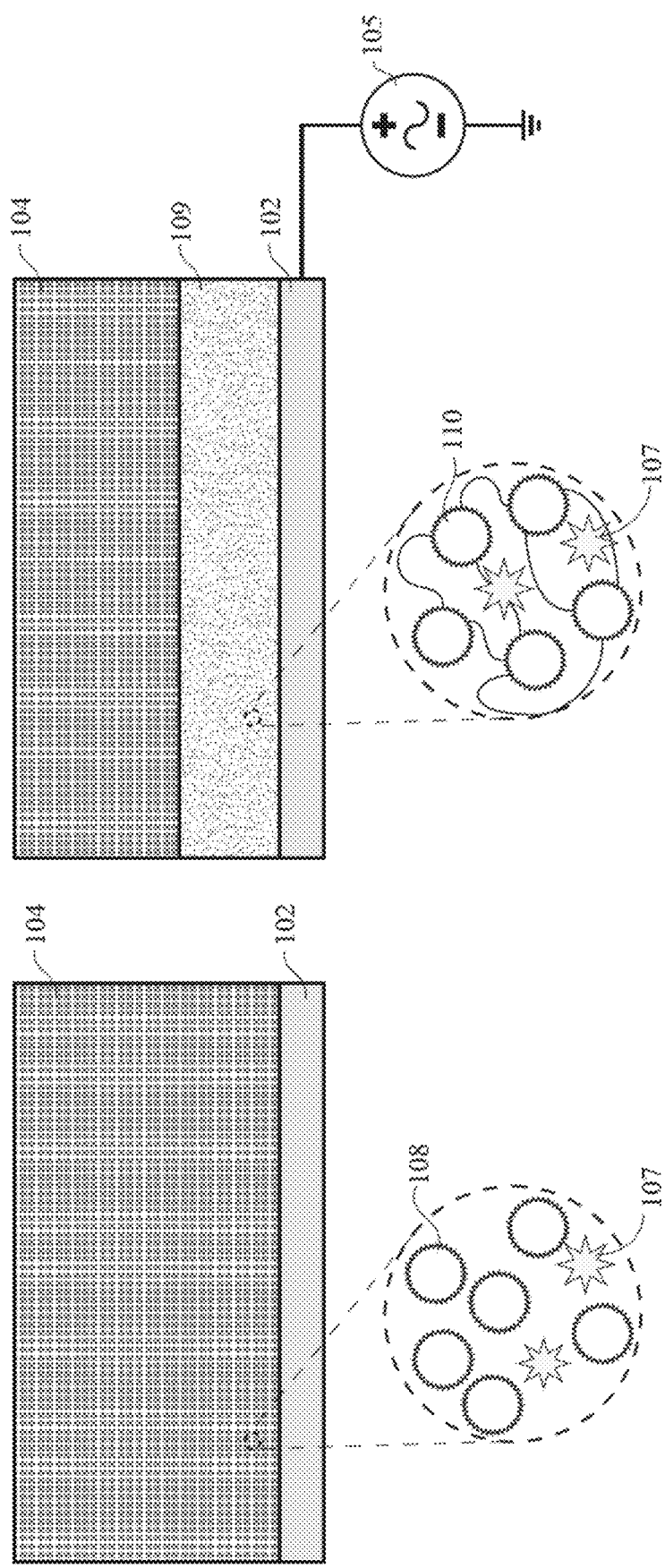
FIG. 9 is a schematic representation delineating the co-electrodeposition of a polymer-biorecognition element film on at least one working electrode of a tissue-penetrating electrochemical sensor.

FIG. 9 is a schematic representation delineating the co-electrodeposition of a polymer-biorecognition element film on at least one working electrode 102 of a tissue-penetrating electrochemical sensor. The working electrode 102 in this example is immersed in a solution 104 comprising at least one of a biomolecular recognition element (107 in inset) and at least one of an organic electroactive monomer precursor (108 in inset) dissolved in said solution. A voltage or current source 105 is connected, in an ohmic fashion, to working electrode 102; a constant or time-varying potential is applied to working electrode 102 to pass a controlled and predetermined amount of current or charge through working electrode 102. This, in turn, instigates the formation of a thin-film, typically on the order of 1-100 nm, of the polymerized organic electroactive monomer (110 in inset), which serves to entrap the biomolecular recognition element to form a co-deposited, highly porous polymer-biorecognition element matrix 109. This processes functionalizes the working electrode 102 of the tissue-penetrating electrochemical sensor 100 and allows it to achieve the selective quantification of at least one chemical or biochemical analyte in a physiological fluid.

McCanna et al., U.S. patent application Ser. No. 14/843,926, filed on Sep. 2, 2015, for a Miniaturized Sub-Nanoampere Sensitivity Low-Noise Potentiostat System is hereby incorporated by reference in its entirety.

Windmiller, U.S. Provisional Patent Application No. 62/233,323, filed on Sep. 26, 2015, for a Methods And Devices For Embedding Sensors In Container Labels and Packaging is hereby incorporated by reference in its entirety.

Windmiller et al., U.S. Provisional Patent Application No. 62/233,324, filed on Sep. 26, 2015, for a Method And System For Manufacturing Microneedles With Electrodes is hereby incorporated by reference in its entirety.

Windmiller et al., U.S. Provisional Patent Application No. 62/247,732, filed on Oct. 28, 2015, for a Method And System For Three Dimensional Printing Of Microneedles And Microneedle Arrays For Transdermal Biosensing And Drug Delivery is hereby incorporated by reference in its entirety.

Windmiller et al., U.S. Provisional Patent Application No. 62/247,730, filed on Oct. 28, 2015, for a Sensors For Wearable Devices is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. Provisional Patent Application No. 62/307,444, filed on Mar. 12, 2016, for a Method And Apparatus For Determining Exhaled Carbon Loss is hereby incorporated by reference in its entirety.

Windmiller, U.S. Provisional Patent Application No. 62/307,445, filed on Mar. 12, 2016, for a Method And System For Determining Physiological and Environmental Strain Indices is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim:

1. A tissue-penetrating electrochemical sensor device for the quantification of a chemical or biochemical entity in a physiological fluid, the device comprising:
    an array of microelectrodes, the array of microelectrodes comprising a working electrode, a reference electrode, and a counter electrode; and
    a polymer film comprising an electroactive monomer precursor and a selective recognition element, the polymer film electro-deposited on at least a portion of the working electrode in response to immersion of the working electrode, the reference electrode, and the counter electrode in a solution and application of a potential applied between the working electrode and at least one of the reference electrode and the counter electrode, the solution comprising
    the selective recognition element, wherein the electroactive monomer precursor is dissolved in the solution, wherein application of the potential occurs during the immersion of the working electrode, the reference electrode, and the counter electrode.

2. The device of claim 1, wherein the electroactive monomer precursor is selected for at least one of its permselective properties following conversion to a thin-film of polymer, its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, and its self-limited growth during conversion to a thin-film of polymer.

3. The device of claim 1, wherein the selective recognition element comprises at least one of an enzyme, a biocatalyst, an inorganic catalyst, an ion-selective material, an antibody, aptamer, an oligonucleotide, an electrochemical redox mediator, a cell, and an organelle.

4. The device of claim 1, wherein the potential is at least one of a fixed potential and a time-varying potential.

5. The device of claim 4, wherein the potential is applied using one of an amperometric technique, a voltammetric technique, a conductometric technique, or a coulometric technique.

6. The device of claim 4, wherein the potential is selected to result in a thickness of the polymer film ranging from about 5 to about 5000 nanometers.

7. The device of claim 4, wherein the potential is applied for a specified time duration to result in a thickness of the polymer film ranging from about 5 to about 5000 nanometers.

8. The device of claim 4, wherein the potential is selected to pass a specified amount of charge through the working electrode to result in a thickness of the polymer film ranging from about 5 to about 5000 nanometers.

9. A method for the fabrication of a tissue-penetrating electrochemical sensor for the quantification of a chemical or biochemical entity in a physiological fluid, the method comprising:
- immersing an array of microelectrodes in a solution comprising a selective recognition element and an electroactive monomer precursor dissolved in the solution, the array of microelectrodes comprising a working electrode, a reference electrode, and a counter electrode;
- applying, during the immersion of the working electrode, the reference electrode, and the counter electrode in the solution, a potential between the working electrode and at least one of the reference electrode and the counter electrode, the application of the potential resulting in electro-deposition on at least a portion of the working electrode of a polymer film comprising the electroactive monomer precursor and the selective recognition element.

10. The method of claim 9, wherein the electroactive monomer precursor is selected for at least one of its perm-selective properties following conversion to a thin-film of polymer, its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, and its self-limited growth during conversion to a thin-film of polymer.

11. The method of claim 9, wherein the selective recognition element comprises at least one of an enzyme, a biocatalyst, an inorganic catalyst, an ion-selective material, an antibody, aptamer, an oligonucleotide, an electrochemical redox mediator, a cell, and an organelle.

12. The method of claim 9, wherein the potential is at least one of a fixed potential and a time-varying potential.

13. The method of claim 12 wherein the potential is applied using one of an amperometric technique, a voltammetric technique, a conductometric technique, or a coulometric technique.

14. The method of claim 12, wherein the potential is selected to result in a thickness of the polymer film ranging from about 5 to about 5000 nanometers.

15. The method of claim 12, wherein to potential is applied for a specified time duration to result in a thickness of the polymer film ranging from about 5 to about 5000 nanometers.

16. A method for the fabrication of a tissue-penetrating electrochemical sensor for the quantification of a chemical or biochemical entity in a physiological fluid, the method comprising:
- immersing an array of microelectrodes in a solution comprising a selective recognition element and an electroactive monomer precursor dissolved in the solution, the array of microelectrodes comprising a working electrode positioned on a first tissue-penetrating electrochemical sensor and at least one additional electrode positioned on a second tissue-penetrating electrochemical sensor;
- applying a voltage ranging from −0.5 volt to +1.5 volt between the working electrode and the at least one additional electrode such that current flows through the working electrode; and
- electrodepositing on the working electrode a polymer film from the electroactive monomer precursor and the selective recognition element, the polymer film having a thickness ranging from about 5 to about 5000 nanometers.

17. The device of claim 1, wherein the selective recognition element and the electroactive monomer precursor are dispersed uniformly and physically entrapped in the polymer film.

18. The method of claim 9, wherein the selective recognition element and the electroactive monomer precursor are dispersed uniformly and physically entrapped in the polymer film.

19. The method of claim 16, wherein the selective recognition element and the electroactive monomer precursor are dispersed uniformly and physically entrapped in the polymer film.

* * * * *

UNITED STATES PATENT AND TRADEMARK OFFICE
CERTIFICATE OF CORRECTION

PATENT NO. : 11,406,818 B2
APPLICATION NO. : 16/666259
DATED : August 9, 2022
INVENTOR(S) : Joshua Windmiller et al.

It is certified that error appears in the above-identified patent and that said Letters Patent is hereby corrected as shown below:

In the Claims

At Column 14, Claim number 15, Line number 4, "wherein to potential" should read "wherein the potential".

Signed and Sealed this
Thirtieth Day of April, 2024

Katherine Kelly Vidal
*Director of the United States Patent and Trademark Office*